United States Patent
Jang

(10) Patent No.: US 6,908,759 B2
(45) Date of Patent: Jun. 21, 2005

(54) METHOD OF MANUFACTURING KIT FOR ISOLATION NUCLEIC ACIDS OR BIOLOGICAL MATERIALS

(75) Inventor: Gi Young Jang, Seoul (KR)

(73) Assignee: Bionex, Inc., Seoul (KR)

( * ) Notice: Subject to any disclaimer, the term of this patent is extended or adjusted under 35 U.S.C. 154(b) by 363 days.

(21) Appl. No.: 10/076,733

(22) Filed: Feb. 14, 2002

(65) Prior Publication Data

US 2003/0082565 A1 May 1, 2003

(30) Foreign Application Priority Data

Oct. 31, 2001 (KR) .......................................... 2001-67742

(51) Int. Cl.[7] ............................ C12M 1/00; C12Q 1/68; G01N 33/53
(52) U.S. Cl. ........................ 435/285.1; 435/6; 435/91.1; 435/92.1
(58) Field of Search .......................... 435/6, 91.1, 91.2; 436/8, 94; 536/23.1, 24.3

(56) References Cited

U.S. PATENT DOCUMENTS

| | | | | |
|---|---|---|---|---|
| 2,970,002 A | | 1/1961 | Laviano ...................... 294/65.5 |
| 3,985,649 A | | 10/1976 | Eddelman .................... 210/42 |
| 4,683,195 A | | 7/1987 | Mullis et al. ................... 435/6 |
| 5,599,660 A | * | 2/1997 | Ramanujam et al. ........... 435/4 |
| 5,861,251 A | * | 1/1999 | Park et al. ...................... 435/6 |
| 6,065,605 A | | 5/2000 | Korpela et al. ............. 209/216 |
| 6,140,110 A | * | 10/2000 | Vinayagamoorthy et al. .... 435/285.1 |

FOREIGN PATENT DOCUMENTS

WO   WO 87/05536   9/1987   ............. B03C/1/00

OTHER PUBLICATIONS

1982 Academic Press Inc., "A Procedure for the Large-Scale Isolation of Highly Purified Plasmid . . .", M. Marko, et al., 6 pages.

(Continued)

Primary Examiner—Kenneth R. Horlick
Assistant Examiner—Heather G. Calamita
(74) Attorney, Agent, or Firm—Blakely Sokoloff Taylor & Zafman

(57) ABSTRACT

The present invention relates to a method of manufacturing a kit for isolating and purifying nucleic acids, or various biological materials, a kit manufactured by the method, and an apparatus using the kit.

The method of manufacturing a kit for isolating or purifying nucleic acids or biological materials from biological samples using solid materials comprises the steps of; fabricating a container having a plurality of chambers and/or column which is configured to contain the solid materials, buffers and/or enzymes suitable for isolation of the nucleic acids or biological materials; fabricating a cover including a protruded portion with a bore formed therethrough; filling each of the chambers or column with the solid materials, buffers and/or enzymes for isolation and purification of the biological materials or nucleic acids; sealing the container with a predetermined sealing material; and packaging the cover and the container, one by one, with a separate case.

According to the present invention, the kit, which is simple, inexpensive and effective in a small or medium number of sample manipulations, can be manufactured. Thus, manual pipetting works by a person who has not fully trained for clinical or biological experiments can be avoided. Further, the disposable kit having the column in which the nucleic acids isolated from the biological samples have been already contained can be directly transferred to the conventional PCR cycler in order to perform the PCR amplification without changing any other buffers and tubes.

17 Claims, 6 Drawing Sheets

OTHER PUBLICATIONS

1995 Academic Press Inc., "A microtiter Plate–Based High–Throughput DNA Purification Method", K. Wang, et al., 6 pages.

Proc. Natl. Acad. Sci USA 76 (1979), vol. 76, No. 2, pp 615–619, Feb. 1979, "Preparative and analytical purification of DNA from agarose", B. Vogelstein and D. Gillespie, 5 pages.

Journal of Clinical Microbiology, Mar. 1990, copyright 1980, p. 495–503, vol. 28, No. 3, "Rapid and Simple Method for Purification of Nucleic Acids", R. Boom, et al.

BioTechniques 22:506–511, Mar. 1997, vol. 22, No. 3, "Rapid, Universal Method to Isolate PCR–Ready DNA Using Magnetic Beads", 6 pages.

BioTechniques 22:554–557, Mar. 1997, vol. 22, No. 3, Rapid Isolation of PCT–Ready DNA from Blood, Bone Marrow and Cultured Cells, Based on Paramegnetic Beads, 4 pages.

* cited by examiner (a)

(b)

(a)

(b)

(a)

(b)

METHOD OF MANUFACTURING KIT FOR ISOLATION NUCLEIC ACIDS OR BIOLOGICAL MATERIALS

BACKGROUND OF THE INVENTION

1. Field of the Invention

The present invention relates to a method of manufacturing a kit for isolating or purifying nucleic acids or biological materials from blood, cells or various biological samples, a kit manufactured by the method, and an apparatus using the kit.

2. Description of the Prior Art

Isolation or purification of nucleic acids from the blood or other various biological samples has been an important starting step in the fields of many areas such as biology, biochemistry, molecular medicine, forensic medicine, medical diagnostics, etc. Recently, a variety of Polymerase Chain Reaction (hereinafter, referred to as "PCR") for DNA amplification (U.S. Pat. No. 4,683,195) have rendered the isolation of nucleic acids from biological samples to be more frequent and essential steps in both research and diagnostic areas. Conventional methods for isolating nucleic acids involve harmful organic solvents such as phenol and chloroform. (Sambrook, J., E. F. Fritsoh and T. Maniatis 1989, Molecular cloning: A Laboratory Manual, 2nd ed., Cold Spring Harbor Laboratory Press, Cold Spring Harbor, N.Y.)

Recently, several methods have been proposed using materials that have the proclivity of binding nucleic acids. Concrete examples of these materials are silica (Boom, R., Sol, C. J. A. Salimans, M. M. M., Jansen, C. L., Wertheim-van Dillen, P. M. E., and van der Noordaa, J. (1990) J. Clin. Microbiol. 28, 495–503), glass fibers (Vogelstein, B., and Gillespie, D. (1979) Proc. Natl. Acs. Sci. USA 76, 615–619; and Marko, M. A., Chipperfield, R., and Birnboim, H. C. (1982) Anal. Biochem. 121, 382–387), anion exchange resins (Wang, K., Boysen, C., and Hood, L. (1995) Anal. Biochem. 226, 85–90) and modified magnetic beads (Rudi, K., Kroken, M., Dahlberg, O. J., Deggerdal, A., Jakobsen, K. S., and Larsen, F. (1997) BioTechniques 22, 506–511; and Deggerdal, A. and Larsen, F. (1997) BioTechniques 22, 554–557).

The advantages of the methods using these materials are that no harmful organic solvents are involved, and that physical and biochemical degrading of nucleic acids during the isolation process is minimized. In addition, immobilized nucleic acids are less susceptible to digestion by nucleic acid-degrading enzymes such as nuclease.

The aforementioned methods, however, still need intensive manual pipetting steps to transfer the solid materials to other vessels, and thus, the performer is vulnerable to potential viral and bacterial infection from infectious viruses and bacteria if infected blood or bacteria is the starting material of nucleic acid isolation.

In order to avoid the intensive and tedious manual steps and to eliminate operator's potential error, several automatic machines such as "MagNa Pure LC" (Roche, Mannheim, Germany AG), "GENESIS" (Techan, Hombrechtikon, Switzerland) and others were developed for a large number of sample manipulations based on the concept disclosed in U.S. Pat. No. 3,985,649. Most of the automatic machines use magnetic beads to collect nucleic acids or biological materials from various biological samples and to eliminate the use of harmful chemical solvents and centrifugation steps. Although these machines are adequate for high throughput isolation of the nucleic acids or biological materials and secure the high throughput, they are also big, expensive, rather complicated, and inefficient for a small or medium number of sample manipulations. As a result, these machines are not practical for most diagnostic clinical and small research laboratories.

Furthermore, in order to operate these machines, the operator should from time to time supply solid materials such as magnetic beads and sufficient buffers to the machines. However, it is cumbersome and difficult for any person who has not trained for biological or clinical experiments to manage the machines.

In addition, the isolated nucleic acids obtained from the conventional machines are not convenient for the PCR amplification since they should be transferred to tubes containing the PCR-ready buffer.

In light of the drawbacks of the conventional machines for isolating nucleic acids or biological materials from the biological samples, there is still a need for a kit and an apparatus which are small, portable and efficiently applicable to the PCR amplification or other biological experiments.

SUMMARY OF THE INVENTION

The present invention is contemplated to solve the above problems in the prior arts.

An object of the present invention is to provide a method of manufacturing a kit for isolating or purifying nucleic acids or biological materials from biological samples, wherein chambers and/or columns are pre-filled with adequate materials such as solid materials, buffers, and/or enzymes.

Another object of the present invention is to provide a disposable kit for isolating or purifying nucleic acids or biological materials from biological samples, wherein chambers are pre-filled with adequate material such as solid materials, buffers and enzymes for biological material isolation.

A further object of the present invention is to provide a disposable kit, wherein chambers and a column are pre-filled with adequate materials such as various solid materials, buffers and enzymes for nucleic acid isolation while also allowing the kit to be easily transferred to and closely fitted into a PCR cycler for PCR amplification after isolation of the nucleic acids, without adding the other buffers or changing the tubes.

A still further object of the present invention is to provide a portable apparatus using the disposable kit for isolating or purifying nucleic acids or biological materials from biological samples, which is less expensive and more readily available to any persons who have not trained for clinical or biological experiments.

According to an aspect of the present invention for achieving the above objects, there is provided a method of manufacturing a kit for isolating nucleic acids or biological materials from biological samples, comprising the steps of fabricating a container including a plurality of chambers which are configured to contain various solid materials, enzyme and buffers suitable for isolation of the biological materials; fabricating a cover including a protruded portion through which a bore is formed and which can dip into each of the chambers of the container, thereby allowing a magnetic bar for picking up the solid materials to pass into the chambers through the bore; filling the chambers with the solid materials, enzymes and buffers for isolation of the biological materials in a predetermined sequence; sealing the container with a predetermined sealing material; and packaging the cover and the container, one by one, with a separate case.

Preferably, according to the method of the present invention, the fabricated container further comprises a column configured to contain the buffer for polymerase chain reaction (PCR), the column being filled with the buffer for performing PCR amplification with the nucleic acids isolated from the biological samples.

According to another aspect of the present invention, there is also provided a kit manufactured by the method.

According to a further aspect of the present invention, there is also provided an apparatus for isolating purifying nucleic acids or biological materials from biological samples using the kit, which comprises a means for upwardly and downwardly moving the cover to mix or agitate buffers, solid materials and enzymes in the respective chambers and column; a means for moving a magnetic bar upwardly and downwardly into the relevant chambers or column through the bore formed in the protruded portion of the cover; a means for moving or positioning the container so that the bore of the cover corresponds to and aligns with the next chamber or column of the container; and a control means for controlling all the means in a predetermined sequence according to processes of isolating the nucleic acids or biological materials from the biological samples and of mixing the isolated nucleic acid or biological materials with pre-filled liquid material for the next experiments.

BRIEF DESCRIPTION OF THE DRAWINGS

The above and other objects and features of the present invention will become apparent from the following description of preferred embodiments given in connection with the accompanying drawings, in which.

DETAILED DESCRIPTION OF THE INVENTION

Figure 1:
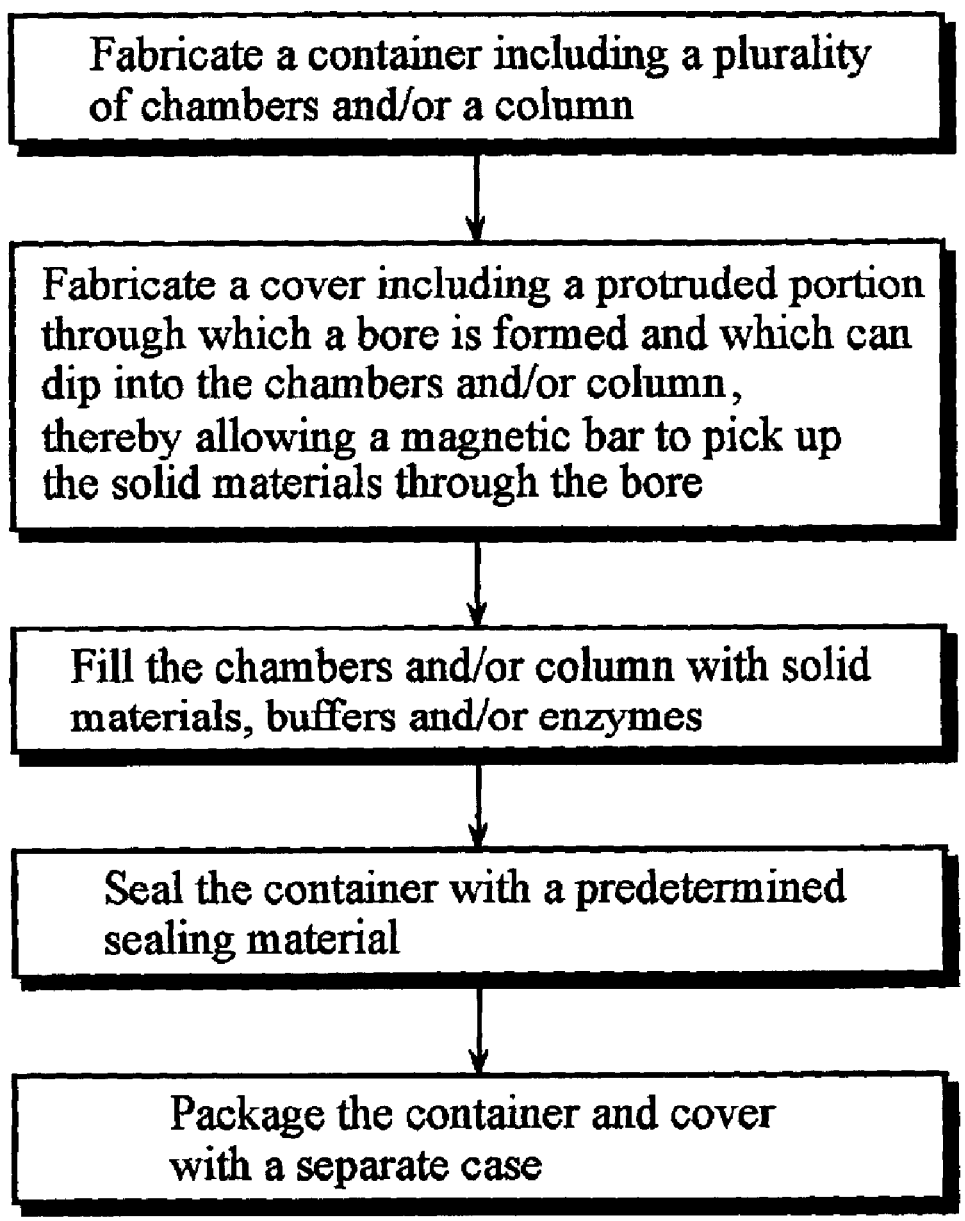
FIG. 1 is a flowchart for explaining a method of manufacturing a disposable kit for isolating or purifying nucleic acids or biological materials from biological samples according to the present invention.

Hereinafter, preferred embodiments of the present invention will be explained in detail with reference to the accompanying drawings.

Referring to FIGS. 1 to 5, a process of manufacturing the disposable kit for isolating nucleic acids or biological materials from biological samples and containing PCR-ready buffers according to the present invention and a kit manufactured by the process are explained in detail.

In the process of manufacturing a kit according to the present invention, a container 10 and a cover 20 constituting the kit are first fabricated.

The container 10 of the kit is constructed to include a plurality of chambers 15 which are configured to contain solid materials and buffers suitable for isolation of the biological materials. In order to define the plurality of chambers 15, the container 10 includes inner and outer walls 11, 12 with a predetermined height H, and a bottom plate 13. A plurality of chambers 15 are formed between the inner and outer walls 11, 12 in such a manner that the inner and outer walls 11, 12 are connected to each other by means of a predetermined number of partitions 16 interposed therebetween and fixed thereto. Each of the chambers 15 of the container 10 is defined by the inner and outer walls 11, 12, the bottom plate 12 and the two adjacent partitions 16. A central hole 14 is defined within the inner wall 11.

The cover 20 of the kit is constructed to include a protruded portion 23 through which a bore 24 is formed and which can dip into the chambers 15 of the container 10. The cover 20 further includes a flat portion 21 and a central shaft 22. The flat portion 21 is made in the form of a base plate from which the central shaft 22 and the protruded portion 23 protrude. The central shaft 22 of the cover 20 can be fitted into the central hole 14 of the container 10 when the cover 20 is in close contact with the container 10. The cover 20 can be raised and lowered with respect to the container 10 in a state where the central shaft 22 is guided along and supported by the central hole 15 of the container 10. The bore 24 is formed through the protruded portion 23 so that a magnetic stick or bar 30 (refer to FIG. 4) can be slid through the bore 24. As described later, the magnetic bar 30 is used to pick up the solid materials in the chambers 15 and to transfer the picked-up solid materials into the next chamber for further processing. Here, the container 10 and the cover 20 are preferably made of polycarbonate, polypropylene, polystyrene, or the like through a molding process.

After the container 10 and the cover 20 have been completely fabricated, the respective chambers 15 of the container 10 are filled with the solid materials and buffers for isolation of the biological materials.

Thereafter, an open top portion of the container 10 with the chambers pre-filled with the solid materials and buffers is sealed with a predetermined sealing material. Preferably, the sealing material is made of aluminum foil, vinyl or plastic wrap, or the like which can prevent the solid material and buffers, which have already filled into the chambers 15, from leaking out. Thus, the disposable kit for isolating biological materials from the biological samples can be manufactured.

Finally, the kit is packaged into a separate case, and thus, the packaged products can be sold.

Figure 3:
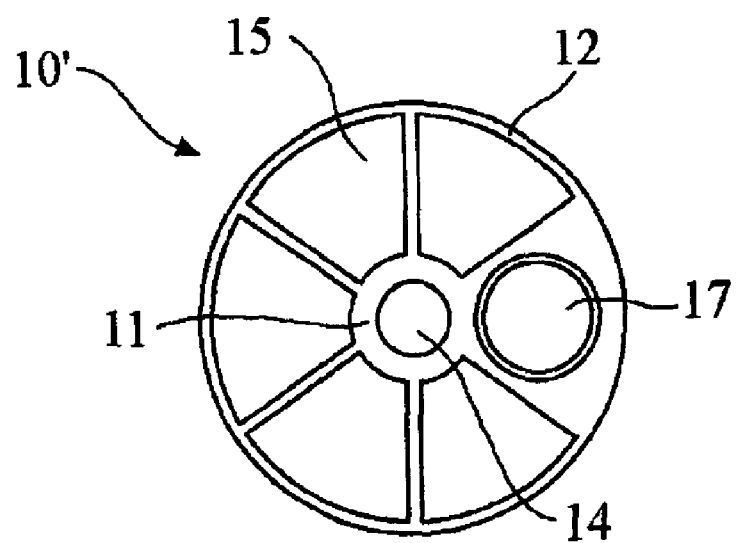
FIG. 3 shows plan and front views of a container of a kit according to a second preferred embodiment of the present invention, respectively, wherein the container includes a plurality of chambers for containing various buffers and magnetic bead materials for isolating nucleic acids from biological samples, and a column for containing PCR buffers composed of enzyme, four kinds of nucleotides dATP, dTTP, dGTP and dCTP, $MgCl_2$, and the like for next PCR amplification.
Figure 3:
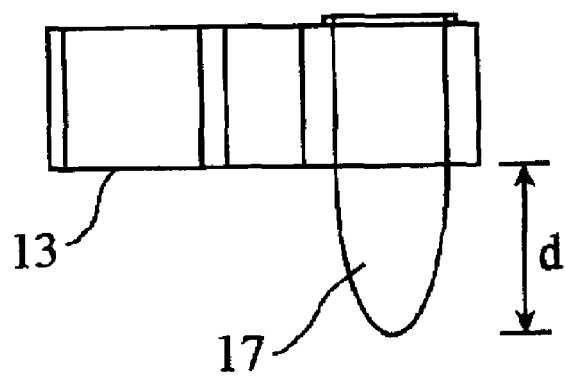
Figure 4:
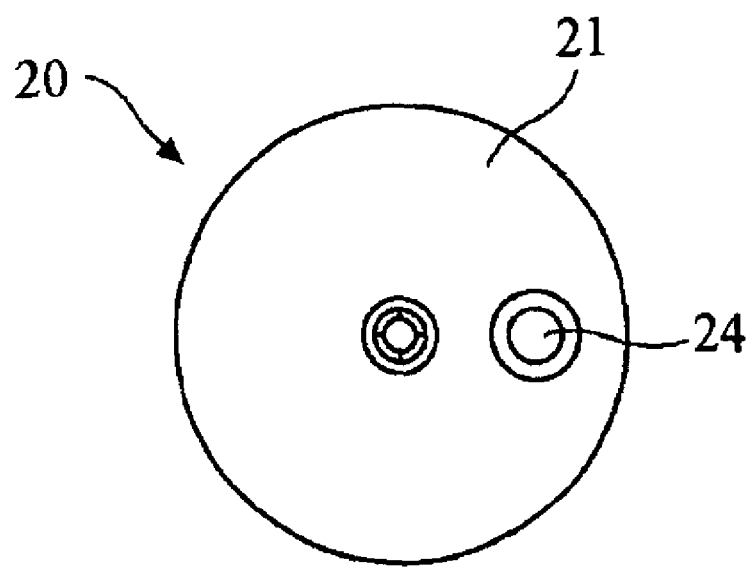
FIG. 4 shows plan and front views of a cover of the kit according to the second embodiment of the present invention, respectively, wherein the kit includes the plurality of chambers and the column.
Figure 4:
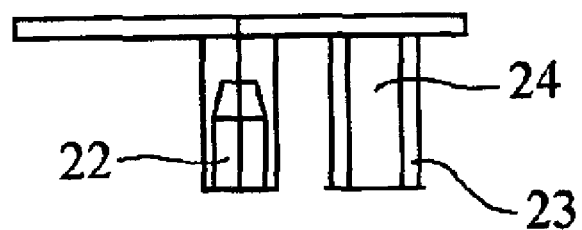

Referring to FIGS. 3 and 4, another embodiment of the method of manufacturing the kit including a container 10' and the cover 20 for use in an application of PCR for nucleic acid amplification is explained. In the preferred embodiment of the present invention, a column 17 is further formed in the container 10'. That is, the column 17 may be formed by further extending one of the chambers 15 downwardly from the bottom plate 13 of the container 10' to a predetermined depth d. Of course, PCR buffers composed of enzymes, four kinds of nucleotides dATP, dTTP, dGTP and dCTP, etc. are contained in the column 17. The column 17 has a configuration that corresponds to a well of the conventional PCR cycler such that the column 17 can be closely fitted into the well of the PCR cycler to be used. As previously mentioned, the column 17 of the container 10' is filled with enzymes and buffer for the PCR, and in such a case, the chambers 15 of the container 10' are, of course, filled with solid materials and buffers for isolation of the biological materials. Thereafter, the container 10' is sealed with the predetermined sealing material, and is then packaged with the separate case. Finally, the disposable kit for isolating the nucleic acids from the biological samples is completed.

Figure 5:
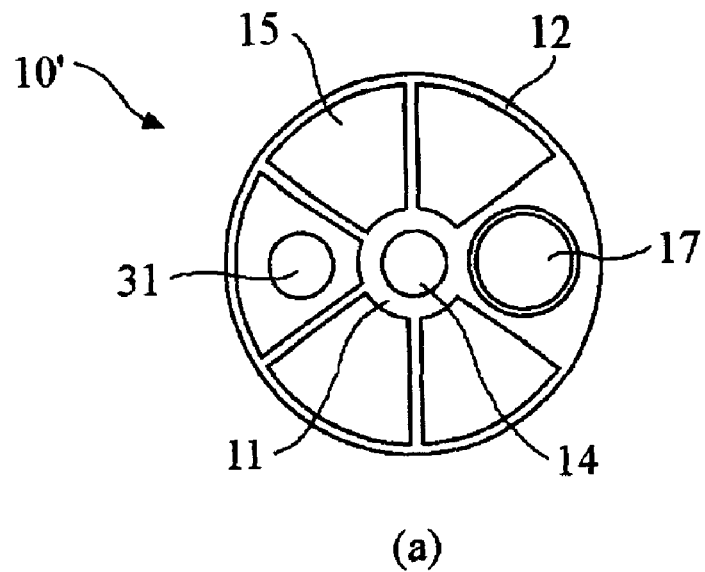
FIG. 5 shows plan and front views of a container of a kit according to a third preferred embodiment of the present invention, respectively, wherein the kit includes a plurality of chambers for containing various buffers, magnetic bead materials and solid materials composed of particles reacting with a magnetic body, and lyophilized PCR components, and a column for containing PCR buffers.
Figure 5:
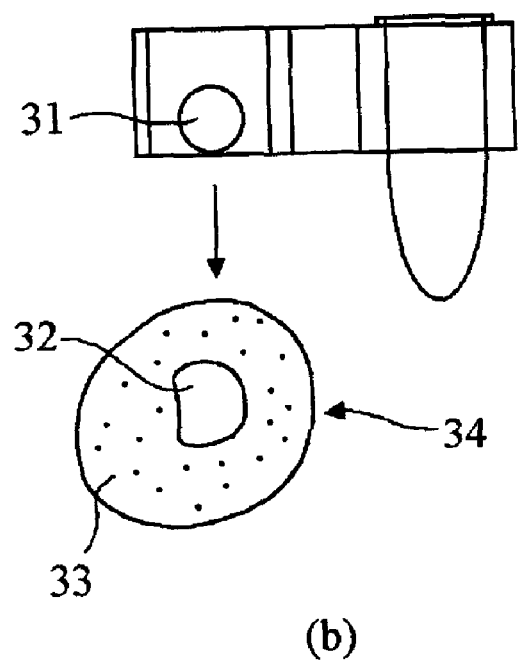

Referring to FIG. 5, a further embodiment of the method of manufacturing a kit including the container and the cover for use in an application of PCR for nucleic acid amplification is explained. In the preferred embodiment of the present invention, at least one of the chambers 15 in the container 10' is specifically configured to contain two different types of the solid materials. One type of the solid materials are magnetic bead materials such that the magnetic bar 30 can pick up the solid materials in a predetermined chamber and transfer the picked-up solid materials to the next chamber. Another type of the solid materials is in the form of a semi-solid material composed of wax, particles reacting with a magnetic body, and lyophilized materials such as lyophilized enzymes and lyophilized primers. More specifically, the solid material 31 is composed of wax 34, particles 32 reacting with the magnetic body, lyophilized PCR components 33 such as enzymes, four kinds of nucleotides dATP, dTTP, dGTP and dCTP, $MgCl_2$, primer and Tris. Of course, the wax may not be included in the solid material 31. The main advantage of using the lyophilized PCR components within the solid material is that lyophilized PCR components are very stable and have very long shelf life. The particles 32 reacting with the magnetic body are either plastics, rubber or similar materials that are magnetized but do not react with the buffers in the chambers, or metals or plastic-coated metallic materials that simply react with the magnetic body but do not react with the buffers in the chambers.

Figure 6:
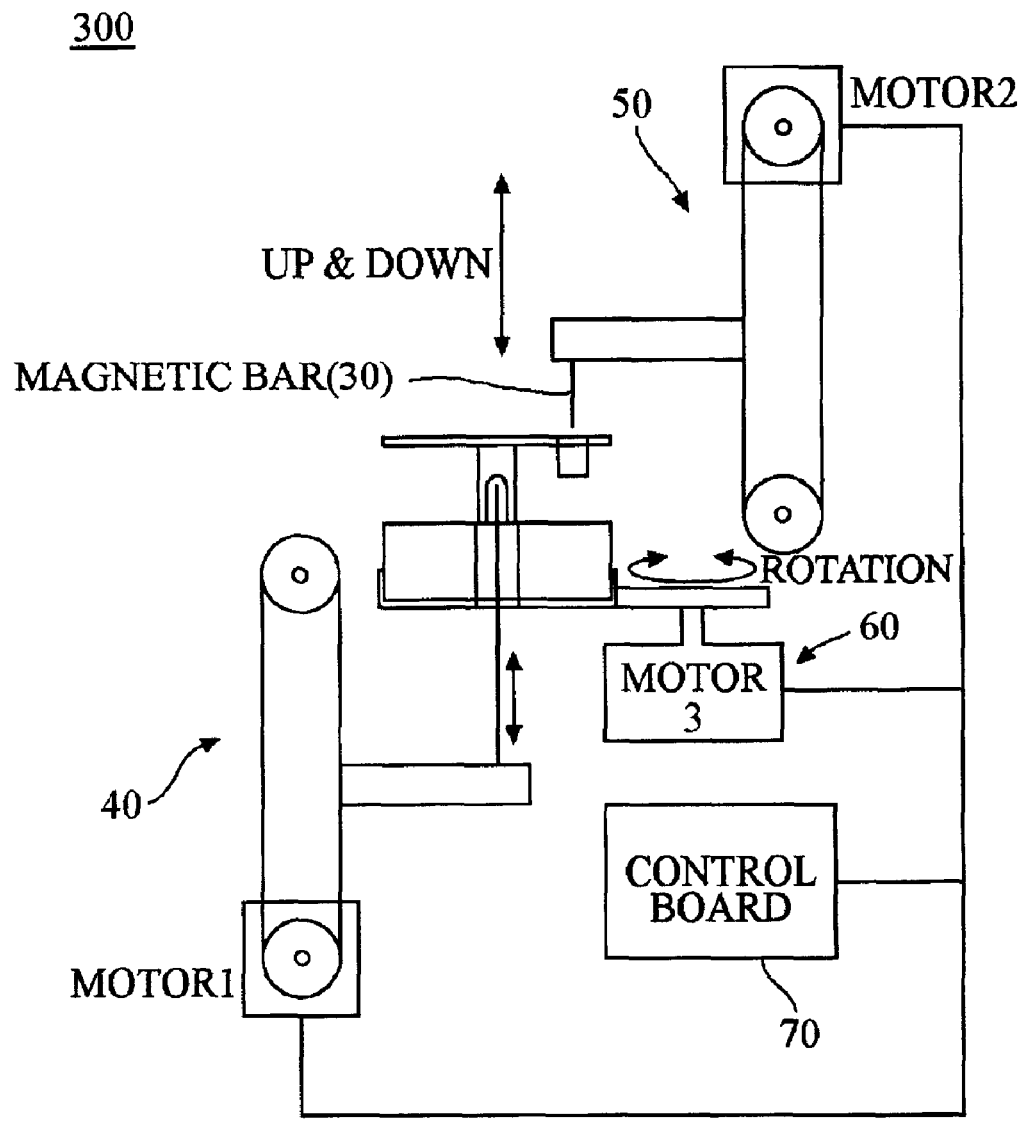
FIG. 6 is a schematic diagram of an apparatus using the disposable kit for isolating or purifying nucleic acids or biological materials from biological samples, according to the present invention.

Next, referring to FIG. 6, an apparatus 300 for isolating the nucleic acids or biological materials from the biological samples in a predetermined order or sequence, using the kit manufactured by the above process, will be described.

The apparatus 300 comprises a means 40 for upwardly and downwardly moving the cover 20, a means 50 for upwardly and downwardly moving the magnetic bar 30 into the chambers 15 or column 17, a means 60 for moving or positioning the container 10 or 10' to a position corresponding to the next chamber or column, and a control means 70 for controlling all the means 40, 50 and 60 in the predetermined sequence.

The cover moving means 40 for upwardly and downwardly moving the cover 20 causes the cover 20 to move upwardly and downwardly by a first motor. As described above, the protruded portion 23 of the cover 20 can dip into the chambers or column when the cover 20 comes into close contact with the container 10 or 10'. Thus, the buffers (i.e., liquid reactants) and solid materials can be efficiently mixed or agitated within the respective chambers 15 by means of the protruded portion 23 through the up and down movement of the cover 20. In order to more efficiently agitate or mix the solid materials and buffers, other means for shaking the container 10 or 10' may be provided.

The magnetic bar moving means 50 for upwardly and downwardly moving the magnetic bar 30 causes the magnetic bar 30 to be inserted into and taken from the relevant chamber or column through the bore 24 of the cover 20 in order to pick up the solid materials in the current chamber and to transfer them into the next chamber or column. Preferably, the magnetic bar moving means 50 may be synchronized with the cover moving means 40. That is, when the cover 20 comes into close contact with the container 10, the magnetic bar 30 is also immersed into the buffer within the chambers 15 and collects the solid materials from the relevant chamber. Then, the cover 20 is raised in a certain degree so that the container 10 can be moved without hindrance of the protruded portion 23 of the cover 20, and the magnetic bar 30 is also raised from the relevant chamber 15 to the same extent or more while picking up the solid materials.

Figure 2:
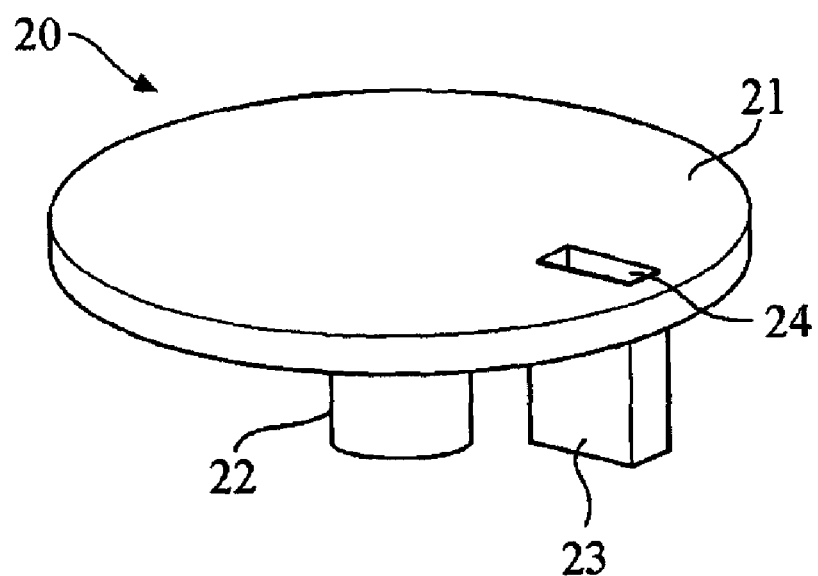
FIG. 2 is an exploded perspective view showing the constitution of the disposable kit according to a first preferred embodiment of the present invention, wherein the kit comprises a cover and a container including a plurality of chambers and a column in which various buffers and magnetized solid materials are contained for isolating the nucleic acid or the biological materials from biological samples.
Figure 2:
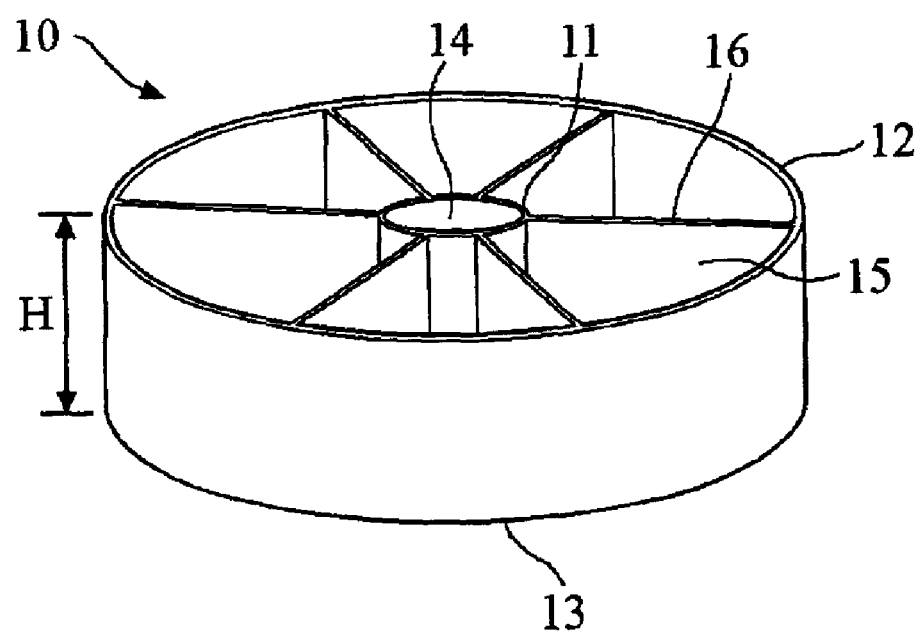

The container moving means 60 for positioning or moving the container 10 or 10' on a worktable (not shown) causes the container 10 or 10' to move from its current operating position to a next operating position where the next chamber or column of the container 10 or 10' aligns with or corresponds to the bore 24 of the cover 20. The container moving means may be manufactured in the form of a moving plate. In a case where the low profile and cylindrical kit shown in FIGS. 2 and 3 is used, it is preferred that the container 10 or 10' be rotated about a central axis of the central hole 14. The container moving means 60 may be connected through a conventional means to a predetermined portion (not shown) of the bottom plate 13 of the container 10 or 10' in order to make the container 10 or 10' be moved to a desired position. The connecting means may be comprised of a recess formed in the predetermined portion and a boss (not shown) that is fitted into the recess and provided in the container moving means 60. Preferably, the container moving means 60 is constructed to include a gear system or belt system for rotating the container 10 or 10'. The container moving means 60 allows the container 10 or 10' to be rotated about the central axis of the central hole 14 by a predetermined angle corresponding to a value, 360/(the total number of chambers and column, if any). Of course, the container moving means 60 may be rotated by a third motor.

Furthermore, a control means 70 for controlling all the moving means 40, 50 and 60 in a predetermined sequence or order is also provided. The control means 70 may be a microcomputer. That is, the apparatus of the present invention may be controlled in the following manner. When the cover 20 is in close contact with the container 10 or 10', the protruded portion 23 of the cover 20 is in a state where the portion 23 dips into a first chamber to agitate or mix the buffers and solid materials in the chamber, and then, the magnetic bar moving means 50 causes the magnetic bar 30 to slide into a first chamber through the bore 24 of the cover 20. Thereafter, the magnetic bar 30 collects the solid materials in the first chamber, and is raised together with or separately from the cover 20 while picking up the collected solid materials. Then, the container 10 or 10' is moved or rotated by the container moving means 60 such that a second chamber is located right below the protruded portion 23 of the cover 20. The cover 20 is again lowered into the second chamber to release the solid material into the buffer, and then, the cover 20 is moved up so that the container 10 can be moved or rotated to mix or agitated the solid material inside the buffer. After mixing or agitation, the cover 20 and the magnetic bar 30 are also again lowered into the second chamber to pick up the solid material. The above procedures will be repeated until all the procedures are completed. Thus, final components such as nucleic acids or biological materials are easily obtained in the column or the last chamber. Needless to say, the cover 20 may be rotated or moved instead of movement or rotation of the container 10.

According to the present invention, since the chambers and/or the column are beforehand filled with the buffers, solid materials, and/or enzymes depending on the test purposes, there are advantages in that the kit can be manufactured to be simple, inexpensive and effective in a small or medium number of sample manipulations and that manual pipetting works by a person who has not fully trained for clinical or biological experiments can be completely avoided. Further, the disposable kit with the column in which the nucleic acids isolated from the biological samples is contained can be directly transferred to the conventional PCR cycler in order to perform the PCR amplification without changing any other buffers and tubes.

While the invention has been shown and described with respect to the preferred embodiments, it will be understood by the skilled in the art that various changes and modifications may be made without departing from the spirit and scope of the invention as defined in the following claims.

What is claimed is:

1. A method of manufacturing a kit for isolating nucleic acids or biological materials from biological samples using solid materials, comprising the steps of:

fabricating a container including a plurality of chambers that are configured to contain the solid materials and buffers suitable for isolation of the nucleic acids or biological materials;

fabricating a cover including a protruded portion through which a bore is formed and which can dip into each of the chambers of the container, thereby allowing a magnetic bar to pick up the solid materials through the bore;

filling the chambers with the solid materials and buffers for isolation of the nucleic acids or biological materials in a predetermined sequence;

sealing the container with a predetermined sealing material; and packaging the cover and the container with a separate case, wherein the container is composed of inner and outer walls, a bottom plate and a plurality of partitions, and each of the chambers is defined by the inner and outer walls, the bottom plate and the two adjacent partitions; and wherein the cover further includes a flat base plate and a central shaft configured to be fitted into a central hole which is defined by the inner wall of the container, and the central shaft is guided into and supported by the central hole such that the cover can be moved upwardly and downwardly with respect to the container.

2. The method as claimed in claim 1, wherein the fabricated container further comprises, a column configured to contain buffers for polymerase chain reaction (PCR), the column being filled with the buffers for performing PCR amplification with the nucleic acids isolated from the biological samples.

3. The method as claimed in claim 1, wherein the solid materials are magnetic beads which absorb or carry nucleic acid or biological material.

4. The method as claimed in claim 3, wherein a material composed of particles reacting with a magnetic body, lyophilized enzymes, lyophilized primers, lyophilized MgCl2, and four kinds of lyophilized nucleotides dATP, dTTP, dGTP and dCTP is further contained in at least one of the chambers.

5. The method as claimed in claim 3, wherein a material composed of wax particles reacting with a magnetic body, lyophilized enzymes. lyophilized primers, lyophilized MgCl2, and four kinds of lyophilized nucleotides dATP, dTTP, dGTP and dCTP is further contained in at least one of the chambers.

6. The method as claimed in claim 4, wherein the particles reacting with the magnetic body are magnetized plastics or rubber.

7. The method as claimed in claim 4, wherein the particles reacting with the magnetic body are metals or coated metallic materials.

8. The method as claimed in claim 5, wherein the particles reacting with the magnetic body are metals or coated metallic materials.

9. The method as claimed in claim 5, wherein the particles reacting with the magnetic body are magnetized plastics or rubber.

10. The method as claimed in claim 2, wherein the column has a configuration that a protruded portion of the column can be closely fitted into a well of a PCR cycler.

11. The method as claimed in claim 2, wherein the solid materials are magnetic beads which absorb or carry nucleic acid or biological material.

12. The method as claimed in claim 11, wherein a material composed of particles reacting with a magnetic body, lyophilized enzymes, lyophilized primers, lyophilized MgCl2 and four kinds of lyophilized nucleotides dATP, dTTP, dGTP and dCTP is further contained in at least one of the chambers.

13. The method as claimed in claim 11, wherein a material composed of wax, particles reacting with a magnetic body, lyophilized enzymes, lyophilized primers, lyophilized MgCl2, and four kinds of lyophilized nucleotides dATP, dTTP, dGTP and dCTP is further contained in at least one of the chambers.

14. The method as claimed in claim 12, wherein the particles reacting with the magnetic body are magnetized plastics or rubber.

15. The method as claimed in claim 12, wherein the particles reacting with the magnetic body are metals or coated metallic materials.

16. The method as claimed in claim 13, wherein the particles reacting with the magnetic body are metals or coated metallic materials.

17. The method as claimed in claim 13, wherein the particles reacting with the magnetic body are magnetized plastics or rubber.

* * * * *